(12) United States Patent
Zukowski et al.

(10) Patent No.: US 10,905,576 B2
(45) Date of Patent: ***Feb. 2, 2021

(54) CONTROLLED DEPLOYABLE MEDICAL DEVICE AND METHOD OF MAKING THE SAME

(71) Applicant: W. L. Gore & Associates, Inc., Newark, DE (US)

(72) Inventors: Stanislaw L. Zukowski, Flagstaff, AZ (US); Edward H. Cully, Flagstaff, AZ (US); Keith M. Flury, Flagstaff, AZ (US); Michelle L. Gendron, Flagstaff, AZ (US); Patrick S. Young, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 182 days.

This patent is subject to a terminal disclaimer.

(21) Appl. No.: 15/911,700

(22) Filed: Mar. 5, 2018

(65) Prior Publication Data

US 2018/0193178 A1 Jul. 12, 2018

Related U.S. Application Data

(63) Continuation of application No. 14/531,697, filed on Nov. 3, 2014, now Pat. No. 9,907,683, which is a (Continued)

(51) Int. Cl.
*A61F 2/954* (2013.01)
*A61F 2/07* (2013.01)
(Continued)

(52) U.S. Cl.
CPC ............... *A61F 2/954* (2013.01); *A61F 2/07* (2013.01); *A61F 2/95* (2013.01); *A61F 2/97* (2013.01);
(Continued)

(58) Field of Classification Search
CPC .............. A61F 2/06–07; A61F 2/95–97; A61F 2002/061–077; A61F 2002/9505–9665; A61F 2002/9511
See application file for complete search history.

(56) References Cited

U.S. PATENT DOCUMENTS

| 4,738,666 A | 4/1988 | Fuqua |
| 5,035,706 A | 7/1991 | Giantureo et al. |

(Continued)

FOREIGN PATENT DOCUMENTS

| EP | 0664107 A1 | 7/1995 |
| EP | 0956833 A3 | 5/2000 |

(Continued)

OTHER PUBLICATIONS

International Search Report and Written Opinion from PCT/US2009/003383, dated Sep. 17, 2009, 12 pages.
(Continued)

*Primary Examiner* — Katherine M Shi
*Assistant Examiner* — Lindsey Bachman (57) ABSTRACT

Controlled deployable medical devices that are retained inside a body passage and in one particular application to vascular devices used in repairing arterial dilations, e.g., aneurysms. Such devices can be adjusted during deployment, thereby allowing at least one of a longitudinal or radial re-positioning, resulting in precise alignment of the device to an implant target site.

22 Claims, 6 Drawing Sheets

Related U.S. Application Data continuation of application No. 12/478,245, filed on Jun. 4, 2009, now abandoned.

(60) Provisional application No. 61/058,770, filed on Jun. 4, 2008.

(51) Int. Cl.
*A61F 2/95* (2013.01)
*A61F 2/97* (2013.01)
*A61F 2/89* (2013.01)

(52) U.S. Cl.
CPC ............ *A61F 2/89* (2013.01); *A61F 2002/072* (2013.01); *A61F 2002/075* (2013.01); *A61F 2002/9505* (2013.01); *A61F 2002/9511* (2013.01)

(56) References Cited

U.S. PATENT DOCUMENTS

| | | |
|---|---|---|
| 5,387,235 A | 2/1995 | Chuter |
| 5,405,378 A | 4/1995 | Strecker |
| 5,464,449 A | 11/1995 | Ryan |
| 5,554,183 A | 9/1996 | Nazari |
| 5,643,279 A | 7/1997 | Trotta |
| 5,662,702 A | 9/1997 | Keranen |
| 5,683,451 A | 11/1997 | Lenker |
| 5,693,083 A | 12/1997 | Baker et al. |
| 5,713,948 A | 2/1998 | Uflacker |
| 5,776,186 A | 7/1998 | Uflacker |
| 5,800,521 A | 9/1998 | Orth |
| 5,824,055 A | 10/1998 | Spiridigliozzi |
| 5,843,158 A | 12/1998 | Lenker |
| 5,957,929 A | 9/1999 | Brenneman |
| 6,019,785 A | 2/2000 | Strecker |
| 6,042,605 A | 3/2000 | Martin et al. |
| 6,051,001 A | 4/2000 | Borghi |
| 6,168,616 B1 | 1/2001 | Brown |
| 6,235,051 B1 | 5/2001 | Murphy |
| 6,245,097 B1 | 6/2001 | Inoue |
| 6,251,132 B1 | 6/2001 | Ravenscroft |
| 6,270,520 B1 | 8/2001 | Inoue |
| 6,280,464 B1 | 8/2001 | Hayashi |
| 6,287,315 B1 | 9/2001 | Wijeratne |
| 6,302,891 B1 | 10/2001 | Nadal |
| 6,352,561 B1 | 3/2002 | Leopold et al. |
| 6,361,637 B2 | 3/2002 | Martin |
| 6,371,979 B1 | 4/2002 | Beyar |
| 6,416,536 B1 | 7/2002 | Yee |
| 6,520,986 B2 | 2/2003 | Martin |
| 6,533,811 B1 | 3/2003 | Ryan |
| 6,537,284 B1 | 3/2003 | Inoue |
| 6,551,350 B1 | 4/2003 | Thornton et al. |
| 6,558,396 B1 | 5/2003 | Inoue |
| 6,565,597 B1 | 5/2003 | Fearnot |
| 6,656,212 B2 | 12/2003 | Ravenscroft |
| 6,676,692 B2 | 1/2004 | Rabkin |
| 6,723,116 B2 | 4/2004 | Taheri |
| 6,733,521 B2 | 5/2004 | Chobotov et al. |
| 6,740,111 B1 | 5/2004 | Lauterjung |
| 6,776,791 B1 | 8/2004 | Stallings |
| 6,821,291 B2 | 11/2004 | Bolea |
| 6,837,901 B2 | 1/2005 | Rabkin |
| 6,852,116 B2 | 2/2005 | Leonhardt et al. |
| 6,855,159 B1 | 2/2005 | Tanner |
| 6,916,335 B2 | 7/2005 | Inoue |
| 6,945,990 B2 | 9/2005 | Greenan |
| 6,984,244 B2 | 1/2006 | Perez et al. |
| 7,074,235 B1 | 7/2006 | Roy |
| 7,226,473 B2 | 6/2007 | Brar et al. |
| 7,803,177 B2 | 9/2010 | Hartley et al. |
| 7,993,383 B2 | 8/2011 | Hartley et al. |
| 8,043,356 B2 | 10/2011 | Kolbel |
| 8,252,037 B2 | 8/2012 | Styrc et al. |
| 8,361,137 B2 | 1/2013 | Perouse |
| 8,845,709 B2 | 9/2014 | Styrc et al. |
| 9,107,771 B2 | 8/2015 | Wubbeling et al. |
| 9,198,787 B2 | 12/2015 | Kratzberg |
| 9,314,355 B2 | 4/2016 | Styrc |
| 9,375,308 B2 | 6/2016 | Norris |
| 9,427,317 B2 | 8/2016 | Styrc |
| 9,907,683 B2 | 3/2018 | Zukowski et al. |
| 10,219,925 B2 | 3/2019 | Cully et al. |
| 2002/0038144 A1 | 3/2002 | Trout |
| 2002/0099431 A1 | 7/2002 | Armstrong et al. |
| 2002/0161377 A1 | 10/2002 | Rabkin |
| 2002/0161427 A1 | 10/2002 | Rabkin |
| 2002/0188344 A1 | 12/2002 | Bolea |
| 2003/0004560 A1 | 1/2003 | Chobotov |
| 2003/0135257 A1 | 7/2003 | Taheri |
| 2003/0135269 A1 | 7/2003 | Swanstrom |
| 2003/0199966 A1 | 10/2003 | Shiu |
| 2003/0225446 A1 | 12/2003 | Hartley |
| 2004/0044395 A1 | 3/2004 | Nelson |
| 2004/0087965 A1 | 5/2004 | Levine |
| 2004/0093058 A1 | 5/2004 | Cottone |
| 2004/0093063 A1 | 5/2004 | Wright |
| 2004/0138734 A1 | 7/2004 | Chobotov et al. |
| 2004/0143316 A1 | 7/2004 | Spiridigliozzi |
| 2004/0147939 A1 | 7/2004 | Rabkin |
| 2004/0210298 A1 | 10/2004 | Rabkin |
| 2004/0220655 A1 | 11/2004 | Hartley |
| 2004/0230287 A1 | 11/2004 | Hartley et al. |
| 2004/0260383 A1 | 12/2004 | Honda |
| 2005/0038495 A1 | 2/2005 | Greenan |
| 2005/0060018 A1 | 3/2005 | Ditman |
| 2005/0085890 A1 | 4/2005 | Rasmussen |
| 2005/0090834 A1 | 4/2005 | Chiang |
| 2005/0107862 A1 | 5/2005 | Ohlenschlaeger |
| 2005/0119722 A1 | 6/2005 | Styrc |
| 2005/0182290 A1 | 8/2005 | Lau |
| 2005/0182476 A1 | 8/2005 | Hartley et al. |
| 2006/0004433 A1 | 1/2006 | Greenberg et al. |
| 2006/0036314 A1 | 2/2006 | Perez |
| 2006/0155363 A1 | 7/2006 | LaDuca |
| 2006/0184226 A1 | 8/2006 | Austin |
| 2006/0190075 A1 | 8/2006 | Jordan |
| 2006/0229699 A1 | 10/2006 | Tehrani |
| 2006/0259119 A1 | 11/2006 | Rucker |
| 2006/0259122 A1 | 11/2006 | Eliseev |
| 2006/0276872 A1 | 12/2006 | Arbefeuille |
| 2007/0010875 A1 | 1/2007 | Trout |
| 2007/0016281 A1 | 1/2007 | Melsheimer |
| 2007/0043425 A1 | 2/2007 | Hartley |
| 2007/0043432 A1 | 2/2007 | Christensen |
| 2007/0088424 A1 | 4/2007 | Greenberg |
| 2007/0100427 A1* | 5/2007 | Perouse ............... A61F 2/962 623/1.11 |
| 2007/0142894 A1 | 6/2007 | Moore |
| 2007/0225797 A1 | 9/2007 | Krivoruhko |
| 2007/0233223 A1* | 10/2007 | Styrc .................... A61F 2/2439 623/1.11 |
| 2008/0082154 A1 | 4/2008 | Tseng et al. |
| 2009/0048656 A1 | 2/2009 | Wen |
| 2010/0049293 A1 | 2/2010 | Zukowski et al. |
| 2010/0049294 A1 | 2/2010 | Zukowski et al. |
| 2014/0330368 A1 | 11/2014 | Gloss et al. |
| 2019/0192323 A1 | 6/2019 | Cully et al. |

FOREIGN PATENT DOCUMENTS

| | | |
|---|---|---|
| EP | 1842508 B1 | 6/2009 |
| EP | 1923024 A3 | 7/2009 |
| FR | 2896405 A1 | 7/2007 |
| JP | 2005179587 A | 7/2005 |
| JP | 2005537107 A | 12/2005 |
| JP | 2008119481 A | 5/2008 |
| WO | WO-1995001761 A2 | 1/1995 |
| WO | WO-1997003624 A1 | 2/1997 |
| WO | WO-2001060285 A9 | 8/2001 |
| WO | WO-2004021932 A1 | 3/2004 |
| WO | WO-2005/079705 | 9/2005 |
| WO | 2006/005082 A2 | 1/2006 |

(56) References Cited

FOREIGN PATENT DOCUMENTS

| WO | WO-2006134258 A1 | 12/2006 |
| WO | WO-2007025101 A2 | 3/2007 |
| WO | WO-2008029296 | 3/2008 |
| WO | WO-2008042266 A2 | 4/2008 |

OTHER PUBLICATIONS

International Search Report and Written Opinion from PCT/US2009/003400, dated Aug. 21, 2009, 11 pages.
International Preliminary Report on Patentability received for PCT Patent Application No. PCT/US2009/003383, dated Dec. 16, 2010, 8 pages.
International Preliminary Report on Patentability received for PCT Patent Application No. PCT/US2009/003400, dated Dec. 16, 2010, 9 pages.

* cited by examiner

CONTROLLED DEPLOYABLE MEDICAL DEVICE AND METHOD OF MAKING THE SAME

CROSS-REFERENCE TO RELATED APPLICATION

This application is a continuation of U.S. patent application Ser. No. 14/531,697, filed Nov. 3, 2014, now U.S. Pat. No. 9,907,683, issued Mar. 6, 2018, which is a continuation of U.S. patent application Ser. No. 12/478,245, filed Jun. 4, 2009, which claims the benefit of Provisional Application No. 61/058,770, filed Jun. 4, 2008, all of which are incorporated herein by reference in their entireties for all purposes.

BACKGROUND OF THE INVENTION

Field of the Invention

The invention relates generally to devices that are retained inside a body passage and in one particular application to vascular devices used in repairing arterial dilations, e.g., aneurysms. More particularly, the invention is directed toward devices that can be adjusted during deployment, thereby allowing at least one of a longitudinal or radial re-positioning of the device.

Discussion of the Related Art

The invention will be discussed generally with respect to deployment of a bifurcated stent graft into the abdominal aorta but is not so limited and may apply to device deployment into other body lumens. When delivering a stent graft by intraluminal or endovascular methods, it is important to know the precise location of the device in the vasculature. Controlling this precise location is particularly important when the device is intended to be deployed in close proximity to branch vessels or adjacent to weakened portions of the aortic wall. Typical stent grafts used to repair an aortic aneurysm incorporate a proximal (i.e. portion of the stent graft closest to the heart) anchoring system intended to limit longitudinal displacement of the stent graft. Often this anchoring system must be precisely placed to avoid occlusion of a branch vessel or to avoid placement within a compromised and damaged portion of the aortic wall.

An improved delivery system for such stent grafts would include a means for allowing precise longitudinal and rotational placement of the stent graft and anchoring system. The precise position of the stent graft and anchoring system would be adjusted and visualized prior to full deployment of the device. Ideally the delivery system would allow the device to be repositioned if the prior deployment position was undesirable.

SUMMARY OF THE INVENTION

The present invention is directed to a controlled deployable medical device and method of making the same that substantially obviates one or more of the problems due to limitations and disadvantages of the related art.

An embodiment of the present invention provides an apparatus, comprising a catheter having a proximal end portion and distal end portion. A hub can be arranged on a distal end portion of the catheter. A stent member is arranged on the proximal end portion of the catheter, the stent member has an inner surface and an outer surface. The stent can be configured in any suitable manner. In an embodiment of the invention, the stent is configured from multiple turns of an undulating element. Such a stent member can have substantially in-phase undulations. A graft member can be arranged about the stent member. Moreover, an element can be connected to a torsional member, wherein the torsional member is capable of retracting a portion of the element and thereby radially compressing at least a portion of the stent.

In another embodiment, the present invention provides an apparatus substantially as described above, further comprising a tube having a proximal end portion and distal end portion arranged on at least a portion of the substantially tubular shaped stent member, wherein at least a portion of the torsional member extends within a portion of the tube.

BRIEF DESCRIPTION OF THE DRAWINGS

The accompanying drawings are included to provide a further understanding of the invention and illustrate certain aspects of the invention.

In the drawings.

DETAILED DESCRIPTION OF THE ILLUSTRATED EMBODIMENTS

The invention relates generally to a novel medical apparatus that includes a device capable of being retained inside a body passage and in one particular application to vascular devices. More particularly, the invention is directed toward devices that can be adjusted during deployment, thereby allowing at least one of a longitudinal or radial re-positioning. The term distal as used herein denotes a position furthest from the heart, while the term proximal denotes a position closest to the heart.

In an embodiment of the invention, the medical apparatus includes a catheter assembly having a proximal end portion and distal end portion. A hub can be optionally arranged on a distal end portion of the catheter assembly. A stent is arranged on a proximal end portion of the catheter. A graft member can be arranged about at least a portion of the stent. The stent may be self-expandable, balloon-expandable or a combination of self-expandable and balloon-expandable.

In some embodiments, the stents can be used to fix the medical apparatus inside a portion of a patient's anatomy. The stent can be preferably constructed from materials that are flexible and strong. The stent can be formed from degradable bioabsorable materials, biodigestible materials, polymeric materials, metallic materials and combinations thereof. In addition, these materials may be reinforced and/or coated with other materials, such as polymeric materials and the like. The coating may be chosen to reduce acidic or basic effects of the gastrointestinal tract, e.g., with a thermoplastic coating such as ePTFE and the like.

More specifically, the stents can be fabricated according to the methods and materials as generally disclosed in, for example, U.S. Pat. No. 6,042,605 issued to Martin, et al., U.S. Pat. No. 6,361,637 issued to Martin, et al. and U.S. Pat. No. 6,520,986 issued to Martin, et al. For example, stents can have various configurations as known in the art and can be fabricated, for example, from cut tubes, wound wires (or ribbons), flat patterned sheets rolled into a tubular form, combinations thereof, and the like. Stents can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

The stents can be formed into a variety of different geometric configurations having constant and/or varied thickness as known in the art. The geometric configurations may include many conventional stent configurations such as a helically wrapped stent, z-shape stent, tapered stent, coil stent, combinations thereof, and the like. The stents can be formed in a variety of patterns, such as, a helix pattern, ring pattern, combinations thereof, and the like.

Grafts can have various configurations as known in the art and can be fabricated, for example, from tubes, sheets or films formed into tubular shapes, woven or knitted fibers or ribbons or combinations thereof. Graft materials can include, for example, conventional medical grade materials such as nylon, polyester, polyethylene, polypropylene, polytetrafluoroethylene, polyvinylchloride, polyurethane and elastomeric organosilicone polymers.

Stents can be used alone or in combination with graft materials. Stents can be configured on the external or internal surface of a graft or may be incorporated into the internal wall structure of a graft. Stent or stent grafts can be delivered endoluminally by various catheter based procedures known in the art. For example self-expanding endoluminal devices can be compressed and maintained in a constrained state by an external sheath. The sheath can be folded to form a tube positioned external to the compressed device. The sheath edges can be sewn together with a deployment cord that forms a "chain stitch". To release and deploy the constrained device, one end of the deployment cord can be pulled to disrupt the chain stitch, allowing the sheath edges to separate and release the constrained device. Constraining sheaths and deployment cord stitching can be configured to release a self-expanding device in several ways. For example a constraining sheath may release a device starting from the proximal device end, terminating at the distal device end. In other configurations the device may be released starting from the distal end. Self-expanding devices may also be released from the device center as the sheath disrupts toward the device distal and proximal ends.

Details relating to constraining sheath materials, sheath methods of manufacture and stent graft compression techniques can be found in, for example, U.S. Pat. No. 6,352,561 issued to Leopold, et al., and U.S. Pat. No. 6,551,350 issued to Thornton, et al.

The catheter and hub assemblies can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyether block amide or thermoplastic copolyether, polyvinylchloride, polyurethane, elastomeric organosilicone polymers, and metals such as stainless steels and nitinol.

Figure 1A:
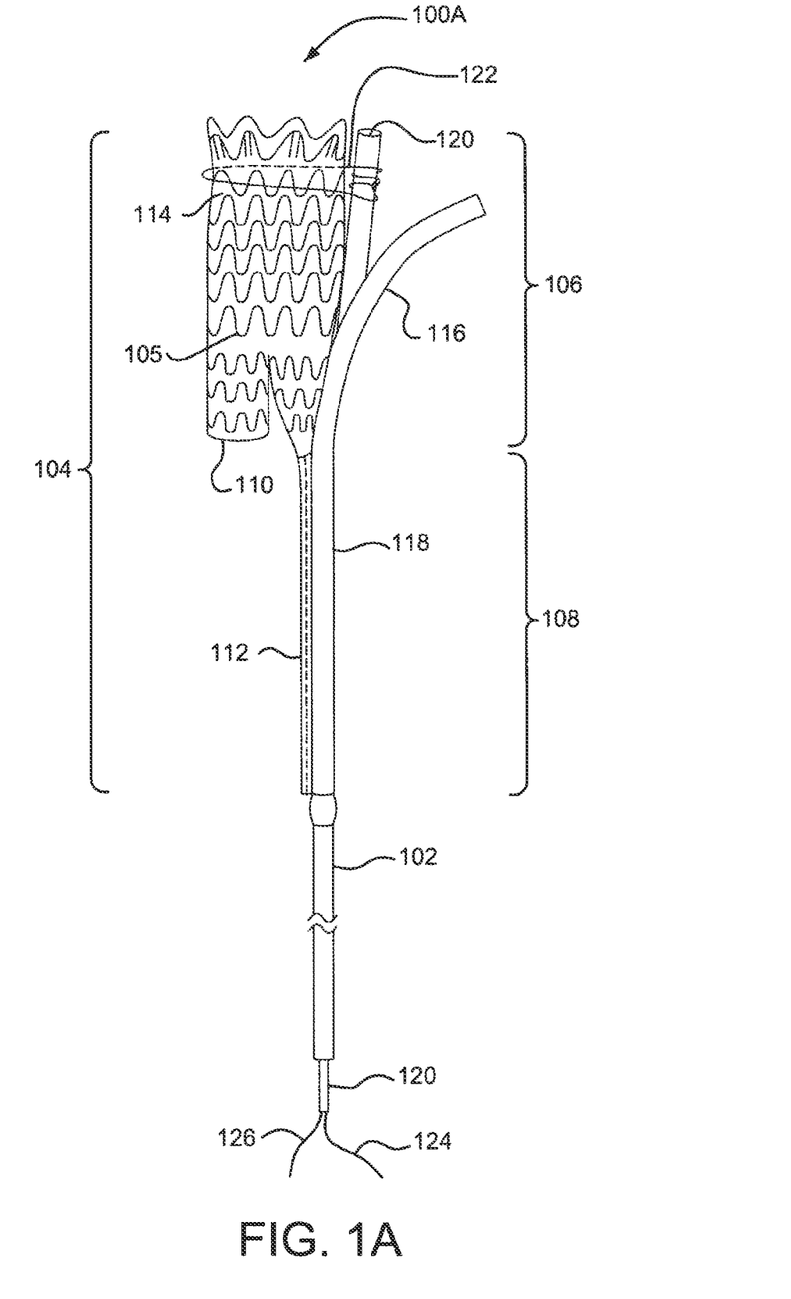
FIG. 1A is a medical apparatus according to an aspect of the invention, having an external torsional member.
Figure 1B:
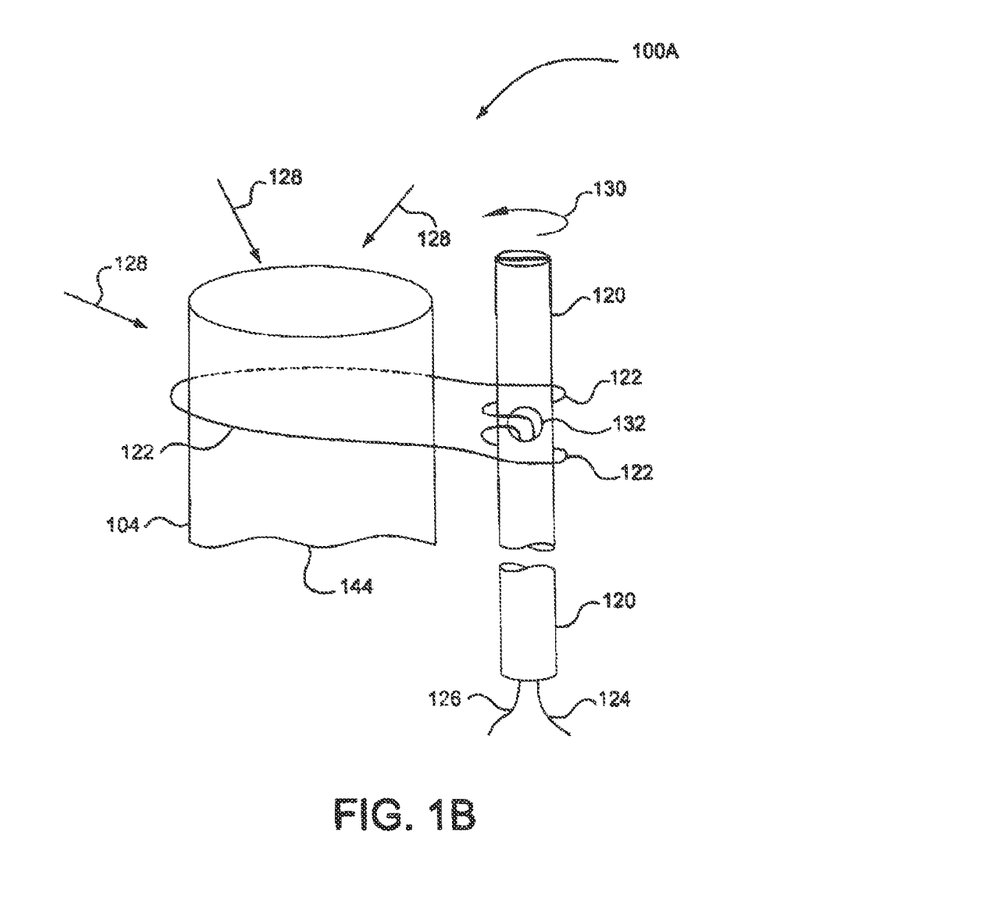
FIG. 1B is an enlarged simplified view of the medical apparatus of FIG. 1A according to an aspect of the invention.

Turning to the figures, FIG. 1A is a medical apparatus according to an embodiment of the invention. FIG. 1B is an enlarged simplified view of a portion of the medical apparatus shown in FIG. 1A.

Referring to FIGS. 1A and 1B, the medical apparatus is generally depicted as reference numeral 100A. The medical apparatus 100A includes catheter assembly 102, stent 104 arranged on the proximal end portion of the catheter assembly 102. The stent 104 has an inner surface, an outer surface, and is configured from multiple turns of an undulating element 105. The undulating element 105 can be configured, for example, in a ring or helical pattern.

The stent 104 has a proximal end portion 106 and distal end portion 108. The distal end portion 108 is formed into a branch having a first leg 110 and a second leg 112.

A graft member 114 is arranged about the stent 104.

In an embodiment of the invention, the stent 104 and graft member 114 are constrained into a compacted delivery state by a first sheath 116 and second sheath 118. As shown in FIG. 1A, the first sheath 116 has been released allowing at least a portion of the stent 104 to expand as shown. The second sheath 118 is coupling the second leg 112 to the catheter assembly 102 as shown.

A torsional member 120 extends from a proximal end portion to a distal end portion of the catheter assembly 102. In the figure, the torsional member 120 is positioned adjacent the outer surface of the stent 104 and graft 114. The torsional member 120 is attached to the catheter assembly 102 and not attached to the stent 104 or graft 114. A movable element 122 having a first end 124 and second end 126 surrounds the stent 104 and graft member 114. The first end 124 and second end 126 of the movable element 122 extend out a distal end portion of the torsional member 120. For example, the movable element 122 is threaded through the tube from a distal end to a proximal end and is looped around the proximal end portion 106 of the stent 104 and graft member 114.

As shown in FIG. 1B, the torsional member 120 can be rotated in the direction shown by arrow 130, tensioning the movable element 122 thereby causing at least a portion of the stent/graft to radial compress in the direction indicated by arrows 128. The torsional member 120 can be configured with a side-wall aperture 132 through which the two ends 124, 126 of the movable element 122 can be routed. The torsional member 120 can be rotated by turning the distal end of the tube 120. The torsional member 120 can be rotated in the opposite direction (of that shown by arrow 130) to allow the stent/graft to expand in the direction opposite of arrows 128. The stent/graft can be compressed to allow rotational or longitudinal displacements within a vessel. When the desired placement is verified, the stent/graft can be allowed to expand and engage the vessel wall. Repeated compressions and expansions of the stent/graft can be utilized as desired. The stent/graft can also be gradually compressed or allowed to gradually expand by varying the amount of twist imparted to the torsional member 120. After final placement of the stent/graft, tension can be applied to one of the ends 124, 126 of the moveable element 122 to release and withdraw the movable element.

Figure 1C:
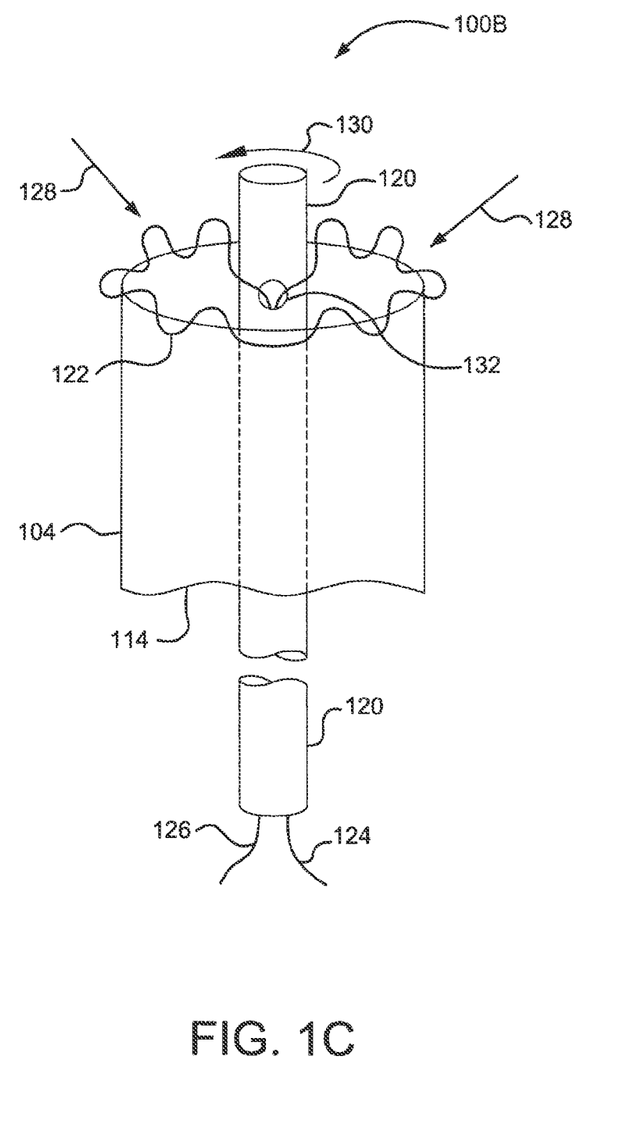
FIG. 1C is a medical apparatus according to an aspect of the invention, having an internal torsional member.

FIG. 1C is a medical apparatus according to a further embodiment of the invention, having a torsional member 120 positioned internal to the stent/graft.

Referring to FIG. 1C, the medical apparatus is generally depicted as reference numeral 100B. The medical apparatus of FIG. 1C is similar to the medical apparatus as shown in FIGS. 1A and 1B. The medical apparatus includes a stent 104 and/or a graft 114 arranged on the proximal end portion of the catheter assembly.

A torsional member 120 extends from a proximal end portion to a distal end portion of the catheter assembly. The torsional member 120 is positioned internal to the stent 104 and graft 114. The torsional member 120 is attached to the catheter assembly and not attached to the stent 104 or graft 114. A movable element 122 having a first end 124 and second end 126 is looped through and around the stent 104 and graft member 114. The first end 124 and second end 126 of the movable element 122 extend out a distal end portion of the torsional member 120. For example, the movable element 122 is threaded through the tube from a distal end to a proximal end and is looped around the proximal end portion of the stent 104 and graft member 114. As shown in FIG. 1C, the torsional member 120 can be rotated in the direction shown by arrow 130, tensioning the movable element 122 thereby causing at least a portion of the stent/graft to radial compress in the direction indicated by arrows 128. The torsional member 120 can be configured with a side-wall aperture 132 through which the two ends 124, 126 of the movable element 122 can be routed. The torsional member 120 can be rotated by turning the distal end of the torsional member 120. The torsional member 120 can be rotated in the opposite direction (of that shown by arrow 130) to allow the stent/graft to expand in the direction opposite of arrows 128. The stent/graft can be compressed to allow rotational or longitudinal displacements within a vessel. When the desired placement is verified, the stent/graft can be allowed to expand and engage the vessel wall. Repeated compressions and expansions of the stent/graft can be utilized as desired. The stent/graft can also be gradually compressed or allowed to gradually expand by varying the amount of twist imparted to the torsional member 120. After final placement of the stent/graft, tension can be applied to one of the moveable ends 124, 126 of the moveable element 122 to release and withdraw the movable element.

Figure 2A:
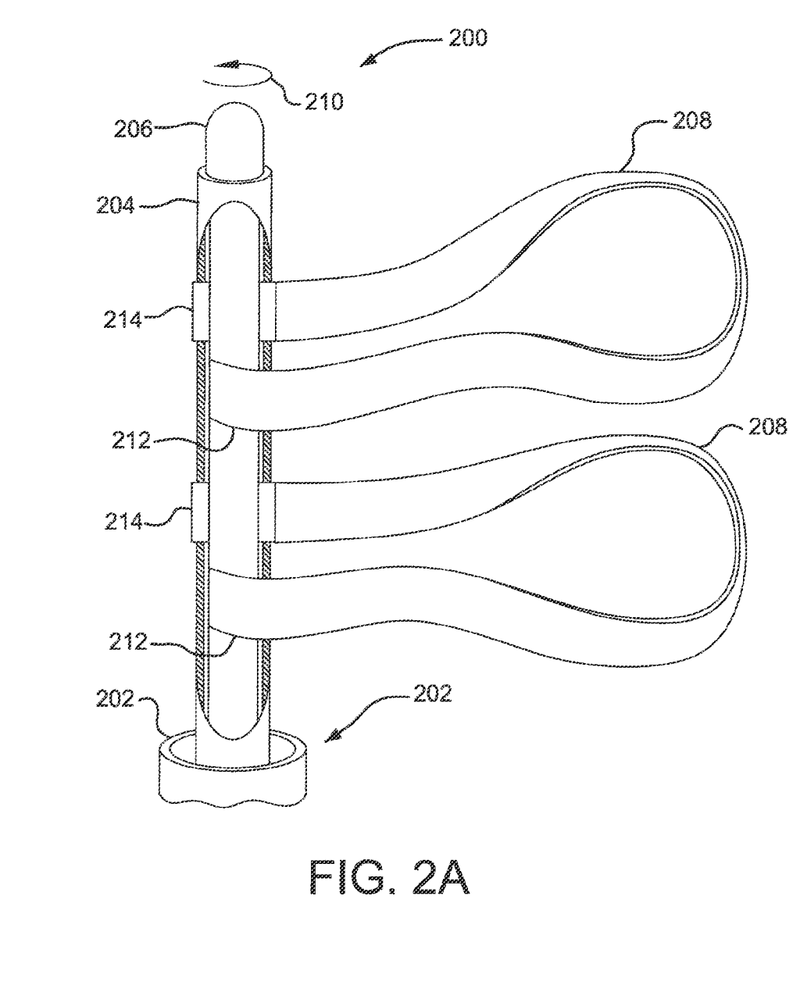
FIGS. 2A and 2B are a medical apparatus according to an aspect of the invention, having flexible straps connected to a torsional member.
Figure 2B:
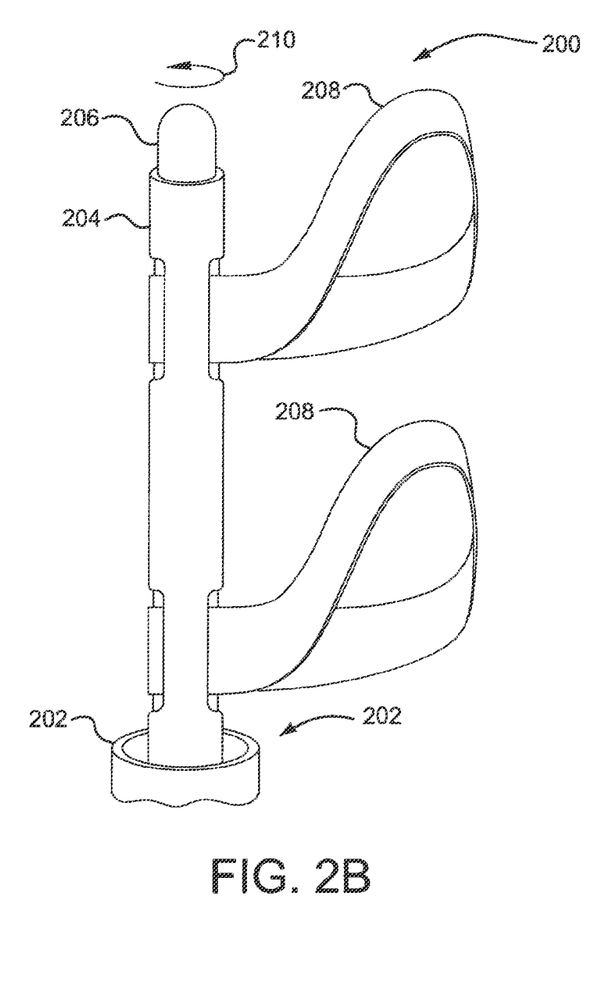

FIGS. 2A and 2B are partial views of the proximal end of a medical apparatus according to a further embodiment of the invention, having releasable straps that can radial compress a stent/graft.

Referring to FIGS. 2A and 2B, the medical apparatus is generally depicted as reference numeral 200. The medical apparatus of FIGS. 2A and 2B is similar to the medical apparatus as shown in FIGS. 1A through 1C with a stent/graft not shown for clarity.

Shown in FIG. 2A is a partial cross-section of a distal end of a catheter system 200 having an outer tube 202. Contained within the outer tube 202 are a first inner tube 204 and a torsional member 206. Attached to the torsional member is at least one flexible strap 208. The flexible strap 208 surrounds a distal portion of a stent/graft (not shown). When the torsional member 206 is rotated as depicted by arrow 210 the strap 208 is further wound around the torsional member 206, thereby "drawing in" the strap which will in turn, compress a surrounded stent/graft. The degree of stent/graft compression can be controlled by varying the amount of twist imparted to the torsional member. A first end 212 of a flexible strap 208 can be affixed to the torsional member 206. The second end 214 of the strap 208 can be wrapped around the torsional member. When the medical apparatus is properly positioned with a target site, the torsional member can be rotated in a direction opposite that shown by arrow 210. This opposite rotation will allow the stent/graft to fully expand. Further opposite rotation of the torsional member will cause the strap end 214 to "un-wind" from the torsional member. The torsional member can then be withdrawn in a distal direction, pulling the strap with attached end 212 into the first inner tube. In an alternate method the first inner tube and the torsional member can be withdrawn together or all three members (204, 206, 208) can be withdrawn together.

Shown in FIG. 2B is a non-cross-sectional perspective view of the distal end of the catheter system shown in FIG. 2A. The flexible straps 208 can be fabricated from various bio-compatible materials as commonly known in the art.

Figure 3A:
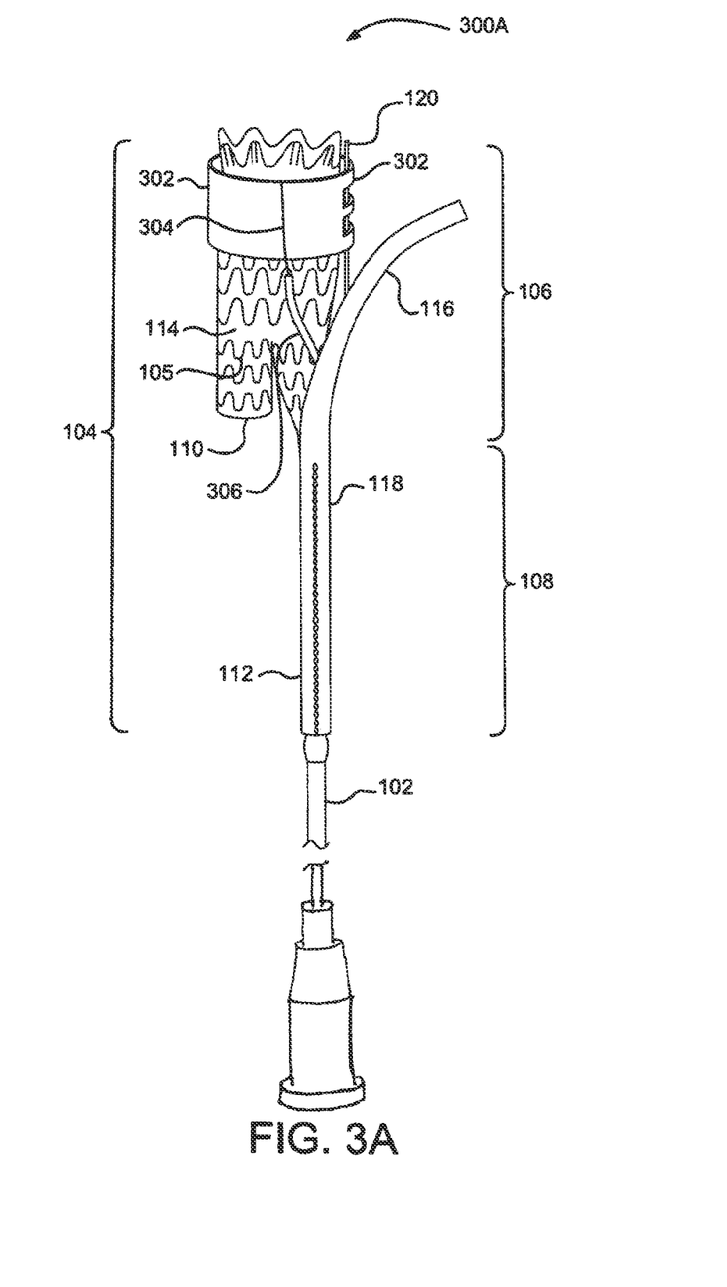
FIG. 3A is a medical apparatus according to an aspect of the invention, having an external torsional member connected to a flexible sleeve with a rip cord.
Figure 3B:
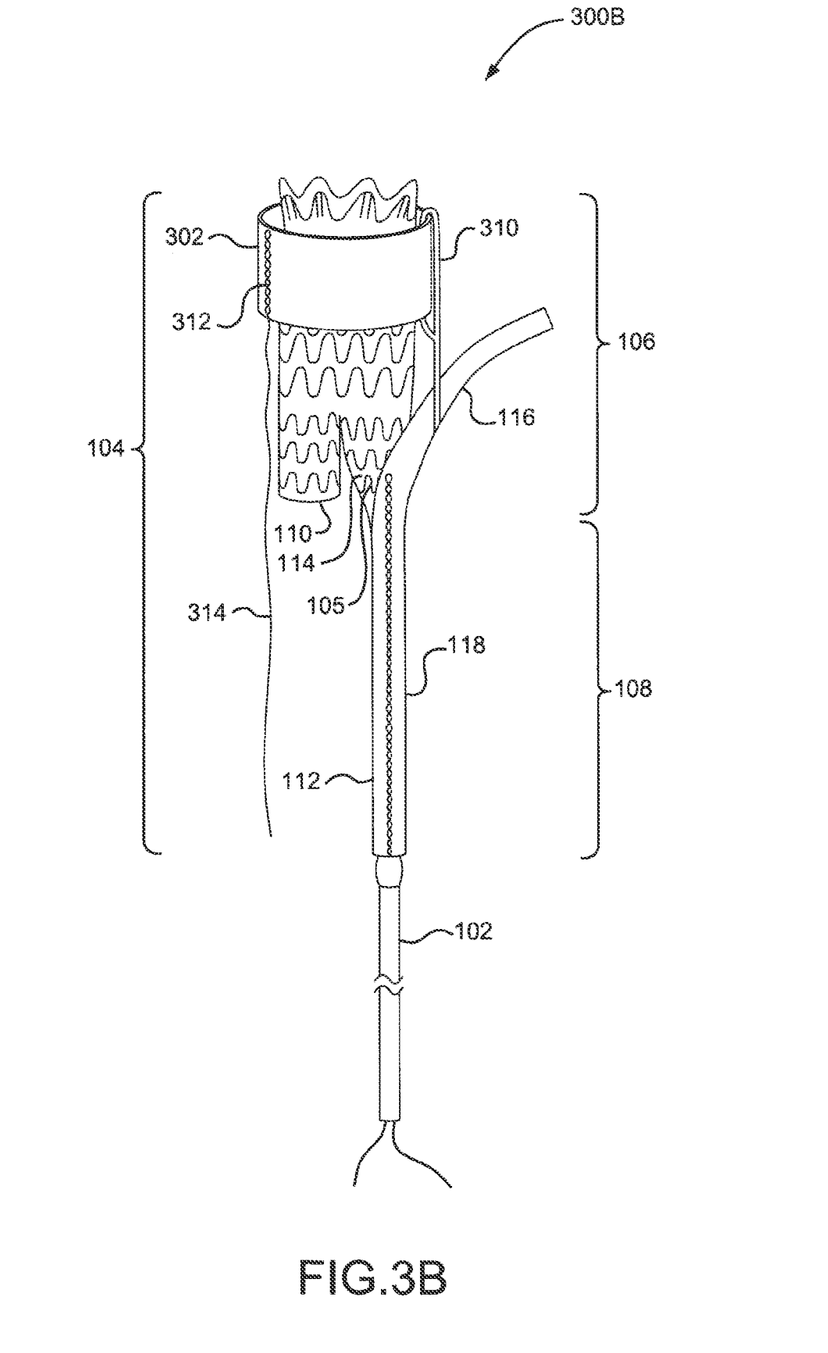
FIG. 3B is a medical apparatus according to an aspect of the invention, having an internal torsional member connected to a flexible constraining sleeve with a parting line.

FIGS. 3A and 3B are partial perspective views of a medical apparatus according to a further embodiment of the invention.

Referring to FIGS. 3A and 3B, the medical apparatus is generally depicted as reference numeral 300A or 300B. The medical apparatus 300A and B includes catheter assembly 102, stent 104 arranged on the proximal end portion of the catheter assembly 102. The stent 104 has an inner surface, an outer surface, and is configured from multiple turns of an undulating element 105. The undulating element 105 can be configured, for example, in a ring or helical pattern.

The stent 104 has a proximal end portion 106 and distal end portion 108. The distal end portion 108 is formed into a branch having a first leg 110 and a second leg 112.

A graft member 114 is arranged about the stent 104.

The stent 104 and graft member 114 are constrained into a compacted delivery state by a first sheath 116 and second sheath 118. As shown in FIGS. 3A and 3B, the first sheath 116 has been released allowing at least a portion of the stent 104 to expand as shown. The second sheath 118 is coupling the second leg 112 to the catheter assembly 102 as shown.

Shown in FIG. 3A is a flexible constraining sleeve 302, surrounding a proximal portion of the stent/graft. A torsional member 120 extends from a proximal end portion to a distal end portion of the catheter assembly 102. In the figure, the torsional member 120 is positioned adjacent the outer surface of the stent 104 and graft 114. The torsional member 120 is attached to the catheter assembly 102 and not attached to the stent 104 or graft 114. The flexible sleeve 302 is attached to the torsional member 120 so that when the torsional member 120 is rotated, the flexible sleeve is compressed which in turn compresses the stent/graft. The flexible sleeve 302 is shown having a parting or rip cord 304. The rip cord 304 can be in the form of a thread or wire that is contained within a secondary tube 306. The secondary tube 306 can exit the distal end of the catheter assembly 102 with the rip cord exiting the distal end of the secondary tube. When the medical apparatus is properly deployed the distal end of the rip cord can be tensioned, thereby ripping or separating the flexible sleeve 302. Since the flexible sleeve is still attached to the torsional member 120, the flexible sleeve 302 can then be withdrawn along with the catheter assembly 102.

Shown in FIG. 3B is a flexible constraining sleeve 302, surrounding a proximal portion of the stent/graft. A torsional member 310 extends from a proximal end portion to a distal end portion of the catheter assembly 102. In the figure, the torsional member 310 is positioned adjacent the outer surface of the stent 104 and graft 114. The torsional member 310 is attached to the catheter assembly 102 and not attached to the stent 104 or graft 114. The flexible sleeve 302 is attached to the torsional member 310 so that when the torsional member 310 is rotated, the flexible sleeve is compressed which in turn compresses the stent/graft. The flexible sleeve 302 is shown having a parting line 312. Shown is a stitched parting line 312 similar to those parting lines incorporated into the first 116 and second 118 sheaths. The release of the stitched parting line 312 can be activated by a release cord 314. The release cord 314 can be in the form of a thread or wire and can be contained within a secondary tube (not shown) or be contained within a catheter system lumen. The release cord 314 can exit the distal end of the catheter assembly 102. When the medical apparatus is properly deployed the distal end of the release cord 314 can be tensioned, thereby un-stitching or separating the flexible sleeve 302. Since the flexible sleeve is still attached to the torsional member 310, the flexible sleeve 302 can then be withdrawn along with the catheter assembly 102.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method of deploying a medical device, comprising:
   providing a catheter having a stent graft arranged on the catheter such that a movable element coupled to a torsional member includes a portion that extends from the torsional member and forms a loop that extends circumferentially about the stent graft, the torsional member positioned exterior to the stent graft;
   advancing the stent graft to a target location within a body of a patient;
   expanding the stent graft from a delivery diameter to an intermediate diameter;
   rotating the torsional member relative to the stent graft to change a dimension of the loop, wherein rotating the torsional member in a first direction causes radial compression of the stent graft, and wherein rotating the torsional member in an opposite second direction allows radial expansion of the stent graft from the intermediate diameter to a deployed diameter;
   releasing the movable element from the stent graft; and
   withdrawing the movable element and torsional member with the catheter from the stent graft.

2. The method of claim 1, wherein expanding the stent graft from the delivery diameter to the intermediate diameter comprises releasing a constraining sheath from the stent graft such that the constraining sheath separates to release the stent graft.

3. The method of claim 2, wherein releasing the constraining sheath from the stent graft comprises withdrawing a cord from the constraining sheath such that the constraining sheath separates to release the stent graft.

4. The method of claim 1, wherein rotating the torsional member in the first direction operates to tension the movable element.

5. The method of claim 1, wherein when the stent graft is constrained to a diameter less than the deployed diameter, rotating the torsional member in the second direction operates to release tension of the movable element which allows radial expansion of the stent graft to the deployed diameter.

6. The method of claim 1, wherein the movable element includes a first end and a second end, and wherein releasing the movable element from the stent graft includes tensioning one of the first and second ends of the movable element.

7. The method of claim 1, wherein the torsional member and the catheter are withdrawn from the stent graft after the movable element is released from the stent graft.

8. The method of claim 1, wherein the movable element includes a strap or a sleeve.

9. The method of claim 1, wherein the movable element extends through a longitudinal lumen of the torsional member.

10. The method of claim 1, wherein the stent graft comprises a stent having an inner surface and an outer surface and a graft member arranged about the stent along at least one of the inner and outer surfaces of the stent, wherein the movable element is arranged circumferentially around the outer surface of the stent.

11. The method of claim 1, wherein the torsional member extends along an outer surface of the stent graft.

12. The method of claim 1, wherein the movable element comprises a bio-compatible material.

13. The method of claim 12, wherein the bio-compatible material comprises a fluoropolymer.

14. The method of claim 13, wherein the fluoropolymer comprises polytetrafluoroethylene or expanded polytetrafluoroethylene.

15. The method of claim 1, wherein rotating the torsional member in the first direction causes the loop formed by the movable element to retract toward the torsional member, and rotating the torsional member in the second direction causes the loop formed by the movable element to extend further from the torsional member.

16. A method of deploying a medical device, comprising:
    providing a stent graft releasably coupled to a movable element, the movable element including a portion that extends from a torsional member and that extends about and surrounds the stent graft to form a loop about the stent graft, the torsional member being positioned exterior to the stent graft and rotatable to change a radial dimension of the loop of the movable element;
    removing a constraining sheath such that the stent graft expands from a delivery diameter to an intermediate diameter;
    rotating the torsional member relative to the stent graft to change the radial dimension of the loop of the movable element, wherein rotating the torsional member in a first direction causes the loop to radially compress the stent graft, and wherein rotating the torsional member in an opposite second direction causes the loop to radially expand such that the stent graft can expand from the intermediate diameter;
    releasing the movable element from the stent graft; and
    withdrawing the movable element and torsional member from the stent graft.

17. The method of claim 16, wherein rotating the torsional member in the first direction operates to tension the movable element and wherein when the stent graft is constrained to a diameter less than a deployed diameter, rotating the torsional member in the second direction operates to release tension of the movable element which allows radial expansion of the stent graft to the deployed diameter.

18. The method of claim 16, wherein the movable element includes a strap or a sleeve.

19. The method of claim 16, wherein the torsional member extends along an outer surface of the stent graft.

20. The method of claim 16, wherein the movable element comprises a bio-compatible polymeric material.

21. The method of claim 20, wherein the bio-compatible polymeric material comprises polytetrafluoroethylene or expanded polytetrafluoroethylene.

22. A method of deploying a medical device, comprising:
- providing a catheter having a stent graft arranged on the catheter such that a movable element coupled to a torsional member includes a portion that extends from the torsional member and forms a loop that extends circumferentially about the stent graft, the torsional member positioned exterior to the stent graft;
- advancing the stent graft to a target location within a body of a patient;
- expanding the stent graft from a delivery diameter to an intermediate diameter;
- rotating the torsional member relative to the stent graft to change a dimension of the loop, wherein rotating the torsional member in a first direction causes radial compression of the stent graft, and wherein rotating the torsional member in an opposite second direction allows radial expansion of the stent graft from the intermediate diameter to a deployed diameter;
- releasing the movable element from the stent graft; and
- withdrawing the movable element and torsional member with the catheter from the stent graft.

* * * * *